United States Patent [19]

Garman

[11] Patent Number: 4,672,958
[45] Date of Patent: Jun. 16, 1987

[54] QUICK RELEASE INFANT BODY RESTRAINT

[76] Inventor: Catherine E. Garman, Skyline Dr., Box 141A, Reading, Pa. 19606

[21] Appl. No.: 687,298

[22] Filed: Dec. 28, 1984

[51] Int. Cl.$^4$ .............................................. A61F 5/46
[52] U.S. Cl. .................................................. 128/134
[58] Field of Search ............................... 128/134, 133

[56] References Cited

U.S. PATENT DOCUMENTS

| | | | |
|---|---|---|---|
| 2,456,898 | 12/1948 | Strandhagen | 128/134 |
| 2,486,114 | 10/1949 | Cataldo | 128/134 |
| 2,868,194 | 1/1959 | Lee | 128/134 |
| 3,136,311 | 6/1964 | Lewis | 128/134 |
| 3,535,719 | 10/1970 | Murcott | 128/134 |
| 3,536,067 | 10/1970 | Sternagel | 128/134 |
| 4,050,737 | 9/1977 | Jordan | 128/134 |

Primary Examiner—John D. Yasko
Attorney, Agent, or Firm—Leonard M. Quittner

[57] ABSTRACT

A quick release infant body restraint useful in the monitoring of crib death syndrome is disclosed in which the restraint comprises a holding member in the form of an hour glass shaped cloth diaper cover which fits over the lower torso of the infant and which has appended to its upper outer edge portion a duality of transverse restraining tethers for taut attachment to crib walls or the like and Velcro ® pads situated in the holding member corners which, when the holding member is made to encircle the baby, are compressed together matingly and stickingly whereby the baby is restrained and such that an attending observer of the infant may, when signaled to do so, instantaneously release the infant from the holder for transfer to a treatment station by demating the pads.

2 Claims, 5 Drawing Figures

QUICK RELEASE INFANT BODY RESTRAINT

CROSS-REFERENCE

There are no cross-references to, nor are there any related applications.

FEDERALLY-SPONSORED RIGHTS

The invention herein was made without any Federal sponsorship or contribution.

BACKGROUND OF THE INVENTION

1. The Field of the Invention

The field of the invention relates to an improved infant body restraint of the type found useful in monitoring for the symptoms of infant crib death syndrome. During the passive phase of the syndrome, it is desirable to inhibit the motion of a baby in a crib or other bed in order to facilitate the attachment to the baby of sensors and leads which connect to an electronic monitor which measures respiratory and cardiological information. The active phase of crib death syndrome presents a medical emergency in which the monitor emits a signal indicating respiratory or cardiac arrest and requires an attendant to release the child virtually instantly from the restraint for transfer to a treatment station.

2. Description of the Prior Art

The prior art, or near or related art, all of which is reaildy distinguishable from the present invention, is best demonstrated by three major approaches to infant body restraint none of which solve the problems created by the unique monitoring requirements of infant crib death syndrome, the treatment for which is much better understood medically than heretofore.

The first major type of device may best be described as a vest or upper body restraint. Such is typified by U.S. Pat. Nos. 4,117,840 to Rasure; 3,788,309 to Zeilman; 3,641,997 to Posey; 3,536,067 to Sternagel; 3,265,065 to Jillson; 2,868,194 to Lee and 2,102,281 to Pringle. Each has the disadvantage of interfering with the sensors which are installed on the infant's upper torso as part of the protocol for anticipating the onset of crib death symptoms. Other disadvantages and drawbacks of this type, common to the other types, will be discussed below.

The second major type of device may be described as a belt restraint fitted around the infant's waist and to the bed. such is typified by U.S. Pat. Nos. 3,742,945 to Reinhard and 2,332,035 to Wickman. These are not amendable to nor do they teach, instant detachment of the baby from the crib because of the limitations inherent in belt to crib design and also because belts may interfere with secure sensor attachment and inspection.

The third type of device is best described as a lower torso restraint as demonstrated in U.S. Pat. Nos. 3,566,864 to Garrow; 2,486,114 to Cataldo and 2,456,898 to Strandhagen. It is in the light of the art of this category that the present invention is best viewed.

The invention is also understood by examining the medical management method which has developed to arrest the syndrome. A baby who is a candidate for close observation, generally in the age group of new born to almost one year, is fitted with sensors adhered to its upper torso which send by means of wire leads respiratory and cardiological information in the form of electrical signals to an analyzing device or monitor to which they are connected. Typical of this apparatus is the Healthdyne Baby Monitor, among others. Under circumstances which indicated that the baby is likely to be entering the active phase of the syndrome, i.e., respiratory or cardiac arrest, the monitor sounds an alarm. The observing attendant is then afforded an opportunity, during a time interval measured in but a few seconds, to transfer the baby from its crib to a firm work surface treatment station upon which the baby has administered to it procedures akin to well-known CPR techniques.

One skilled in the art of attending a baby suspected of infant death syndrome recognizes that unrestrained infant movement can cause the sensors to become disconnected and, therefore, valueless, or that the leads can become entangled around the baby thereby causing injury, even that which may be life threatening. Selective restraint is essential. However, restraint itself, while it must be effective, can not be so restrictive as to cause the attendant to lose vital seconds in undoing it prior to the transfer required at the beginning of the active phase nor so to inhibit in the passive phase substantially all movement which may itself enhance the possibility of triggering the syndrome.

Ideally, restraint of the lower torso will provide ready access to the sensors by the attendant; should provide maximum, safe freedom of leg and arm movement essential to the well-being of the infant but not interfere with the sensors and leads; must appropriately secure the infant to the crib; must permit positioning of the infant on its chest or stomach without the need to reset the crib-to-child restraint and must, above all, provide instant release means of the child upon the signaled onset of the symptoms by the monitor.

Nothing in the prior or related art addresses the foregoing requirements for managing an infant crib death candidate satisfactorily which the present invention does by providing sufficient restraint with simple, quick release.

SUMMARY OF THE INVENTION

The invention is summarized as comprising a lower torso restraining device consisting of a lower torso holding member in the form of a cloth diaper cover which fits over a conventional diaper affixed to the pelvic region of a baby, but leaves entirely uncovered the baby's upper torso from just below the waist upward, in combination with a restraining belt member. The holding member which is essentially an hour glass shaped cloth sheet, has a body-side or inner surface and an outer surface, a top portion, a bottom portion and side edge portions which have conventionally sewn therein elastic material in the vicinity of leg apertures which form when the holding member is enfolds the baby's pelvic region. Sewn along the edge of the top portion's outer surface from the center of the top portion outboard to a defined distance from an angle formed by the top portion and side edge portion, which intersect to form a free corner, is an elongated, rectangular restraining belt member made of cloth such that those portions a substantial distance past the free corners form a duality of restraining tethers one on each end of the best member. The tethers have affixed to their outer ends loop forming means for attachment to uprights of the side rails of a crib in which the baby is placed.

In use, the holding member, body surface up, is laid out on a crib's sleeping surface with the tethers stretched tautly and transversely across the sleeping surface and securely looped around uprights in the crib side rails. The baby is then placed on its back or on its stomach over the holding member whose lower portion, which has rectangular Velcro ® pads sewn on the obverse surface in the corners formed by the intersection of the bottom portion with the side edges. The lower portion is then folded upwardly through the baby's crotch to enwrap its pelvic region and joins at the free corners by means of Velcro ® pads sewn in the free corners on the body surface outboard of where the tethers leave off. The free corner pads and the obverse corner pads are meshed together, matingly and stickingly to hold the baby's body. The taut belt in conjunction with the holding member provides appropriately limited body movement. The Velcro ® pads, in addition to providing firm jointure at the corners of the enwrapped holding member also provide positive release instantly by simply unmeshing the mating Velcro ® surfaces manually. It has been found by experimentation that pins, snaps, hooks, buttons, zippers and other similar corner joining means are not satisfactory to insure a snug fit at the waist and insure the positive instantaneous release required when the monitor signals that the active phase of the syndrome is in progress.

An object of the present invention is to provide a lower torso restraint which will generally inhibit transverse motion or rolling over without injury to a baby hooked up to the monitor by means of the sensors and leads yet to provide natural freedom of arm and leg movement essential to the baby's well-being.

A further object of the invention is to provide means by which the baby may be installed restrainingly in the holding member on its back or stomach without readjustment of the device.

Another object of the invention is to provide visual access to the sensors yet prevent the leads from entangling the baby and doing it injury and also preventing the baby from disconnecting the sensors.

Yet another object of the invention is to permit instant removal of the baby from the restraint, regardless of the baby's position, when signaled by the monitor to commence preventive treatment.

Other objects, advantages and features of the present invention will be apparent to those skilled in the art from the following description taken in conjunction with the accompanying drawings.

DESCRIPTION OF DRAWINGS

The present invention may be better understood by reference to the drawings wherein five (5) figures are shown on one (1) sheet. The numbers shown on the drawings for the various parts of the invention are consistent throughout so that a number indicating a part in one drawing will indicate the same part in another drawing.

DESCRIPTION OF THE PREFERRED EMBODIMENT

Figure 5:
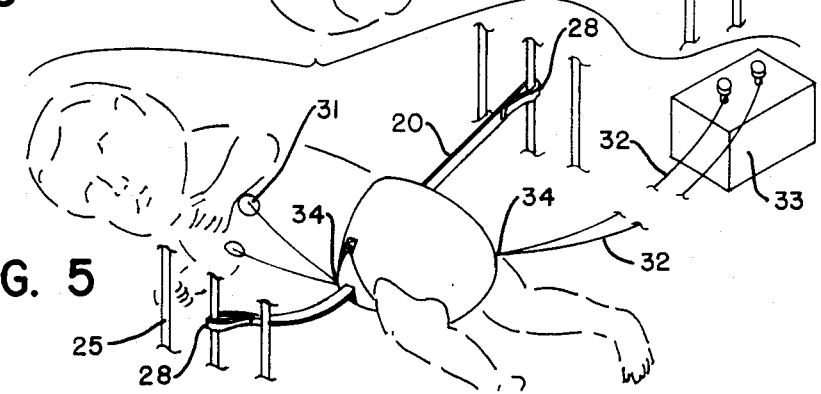
FIG. 5 shows the same installation but with the baby on its stomach.

The preferred embodiment is described as consisting of a cloth lower torso restrain (10) in the form of an hour glass shaped diaper cover with restraining tethers. The restraint comprises a lower torso holding member (11) having an inner, body-side surface (12); an outer, obverse surface (13); an upper portion (14); a lower portion (15) which completes encirclement of the waist when folded upward (16); and side edges (17) having sewn therein an elastic material (18) which forms snug leg apertures (19) when the lower portion is folded upward through a baby's crotch to meet the upper portion. Sewn along and attached to the upper portion is an elongated, rectangularly shaped transverse cloth belt member (20) which is sewn (21) centrally along the edge of the upper portion such that the belt forms a duality of restraint tether portions (22, 23) which lie flat on a crib sleeping surface (24) and project transversely toward the sides of a crib (25) with uprights (26). Each tether, near its free end, has installed thereon connecting means (27) which enable the formation of a loop (28) around a crib upright. The belt member is attached to the obverse surface of the upper portion of the holding member such that a blank region (29) is created on the belt contiguous to a free corner (30) formed by the upper portion's intersection with the side edge. The unattached region allows a certain amount of desirable transverse movement such as torso twisting, as is depicted generally in FIG. 5, and provides space for a quick disconnect jointure of the holding member as described hereinafter.

Figure 1:
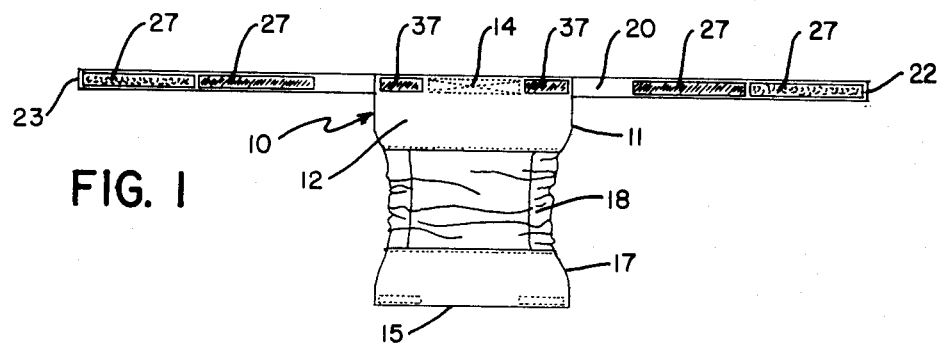
FIG. 1 shows the restraint device, body surface up, as it is laid out on the upper surface of a crib mattress prior to attachment.
Figure 2:
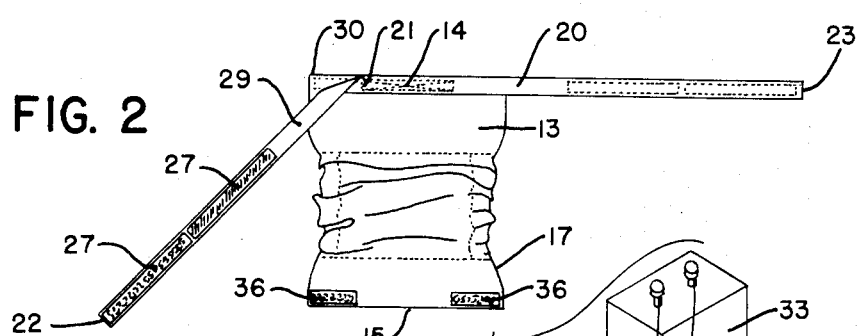
FIG. 2 shows the obverse surface of the device indicating how the restraining belt member is attached to the holding member so as to form tethers and free corners on the top portion.
Figures 3, 4:
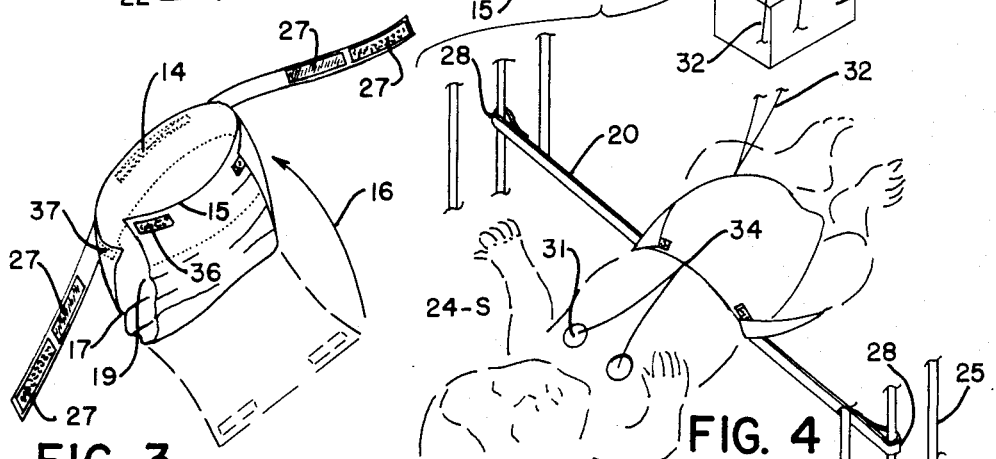
FIG. 3 shows how the lower portion of the holding member is folded upward matingly to mesh the Velcro ® pads and form leg apertures.
FIG. 4 shows complete installation of the device with a baby on its back with sensors attached to the monitor.

In use, the tethers are looped transversely apart tautly across the crib (FIG. 4 and FIG. 5) leaving the holding member laid out flat, body-side surface up on the sleeping surface. A baby with sensors (31) adhered to its chest and connected by wire leads (32) to a monitor (33) may be placed stomach up (FIG. 4) or stomach down (FIG. 5) without interfering with the tethers. The leads are brought adjacent to each other and are automatically secured snugly and compressingly from disconnecting movement when led through the holding member (34) to the monitor when the lower portion of the holding member is drawn up through the baby's crotch (35) and joined snugly to the upper portion to complete encirclement below the waist. Rectangular Velcro ® pads (36) sewn on the body-side surface of the holding member in corners formed by the intersection of the side edges and the bottom portion are then compressingly enmeshed matingly and stickingly to mating Velcro ® pads (37) sewn in the free corners of the upper portion on the observe side thereby enabling jointure at the corners of the holding member around the lower torso yet enabling the pads to be quickly released from each other simply by manual unmeshingly as the baby is quickly removed, leads still in place, to work surface for treatment.

Since many modifications, variations and changes in detail may be made to the presently described embodiments, it is intended that all matter in the foregoing description and accompanying drawings be interpreted as illustrative and not by way of limitation.

What is claimed is:

1. An improved, quick release, lower torso restraining device useful in monitoring the symptoms of infant crib death syndrome in combination comprising
   (a) an hour glass shaped lower torso holding member made of cloth having an inner, body-side surface; an outer, obverse surface; a top portion; a bottom portion and side edge portions; and having
   (b) sewn along the upper portion's edge on the obverse surface by stitch means beginning centrally therefrom, an elongated, rectangularly shaped transverse cloth belt member having restraining tether portions at each end thereof, the stitch means ending a defined distance from the upper portion's intersection with the side edges which form free corners in the upper portion to form unattached regions in the belt contiguous thereto and onto whose
   (c) holding member's free corners are sewn rectangular top pads of Velcro ® on the body surface thereof which are compressingly enmeshed to and mate stickingly with rectangular bottom pads of Velcro ® sewn on the obverse surface of the holding member in corners formed by the bottom portion's intersection with the side edges when the bottom potion is folded upward through the baby's crotch to enwrap the lower torso thereby restraining the infant and quickly releasing the infant from the holding member by manually unmeshing the pads.

2. An improved quick release, lower torso restraining apparatus for use with an electrically driven infant death syndrome monitoring device with wire leads leading therefrom to sensors for attachment to an infant in combination comprising:
   a. an hour glass shaped lower torso holding member made of cloth having an inner, body-side surface; an out, obverse surface; a top portion; a bottom portion and side edge portions; whereby the holding member also hold snugly and immobily on the lower torso the monitor wire leads and having
   b. sewn along the upper portion's edge on the obverse surface by stitch means beginning centrally therefrom, an elongated rectangularly shaped transverse cloth belt member having restraining tether portions at each end thereof, the stitch means ending a defined distance from the upper portion's intersection with the side edges which form free corners in the upper portion to form unattached regions in the belt contiguous thereto to permit limited torso rotation transversely a defined number of degrees which maintains the wires and sensors in a sensing position on the torso and onto whose
   c. holding member's free corners are installed quick release fastening means to mate with corners formed by the bottom portion's intersection with the side edges when the bottom portion is folded upward through the baby's crotch to enwrap the lower torso thereby restraining the infant and quickly releasing the infant from the holding member by manually unmeshing the pads.

* * * * *